US006800638B2

(12) United States Patent
Georges et al.

(10) Patent No.: US 6,800,638 B2
(45) Date of Patent: Oct. 5, 2004

(54) TETRAHYDROPYRIDINE DERIVATIVES, THEIR PREPARATION AND THEIR USE AS CELL PROLIFERATION INHIBITORS

(75) Inventors: Guy Georges, Habach (DE); Adelbert Grossman, Eglfing (DE); Olaf Mundigl, Weilheim (DE); Wolfgang von der Saal, Murnau (DE); Tim Sattelkau, Ludwigshafen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 24 days.

(21) Appl. No.: 10/451,757

(22) PCT Filed: Dec. 21, 2001

(86) PCT No.: PCT/EP01/15390

§ 371 (c)(1),
(2), (4) Date: Jun. 23, 2003

(87) PCT Pub. No.: WO02/051842

PCT Pub. Date: Jul. 4, 2002

(65) Prior Publication Data

US 2004/0053960 A1 Mar. 18, 2004

(30) Foreign Application Priority Data

Dec. 23, 2000 (EP) .............................................. 00128487

(51) Int. Cl.$^7$ ........................ C07D 217/04; A61K 31/47
(52) U.S. Cl. ........................ 514/292; 514/307; 546/81; 546/139

(58) Field of Search ............... 546/81.139; 514/292.307

(56) References Cited

U.S. PATENT DOCUMENTS 5,369,108 A    11/1994   Breslow et al.

FOREIGN PATENT DOCUMENTS

| WO | WO 90/02119  | 3/1990  |
| WO | WO 98/07421  | 2/1998  |
| WO | WO 98/15525  | 4/1998  |
| WO | WO 98/55449  | 12/1998 |

OTHER PUBLICATIONS

Hoffman et al., Nucleic Acids Research, 27, pp. 2057–2058 (1999).
Marks et al., J. Natl. Cancer Institute, 92, pp. 1210–1216 (2000).
Graf von Roedern et al., J. Med. Chem., 41, pp. 3041–3047 (1998).
Koyama et al., Blood, 96, pp. 1490–1495 (2000).
Hoshino et al., The Chemistry of Heterocyclic Compounds, 38, pp. 225–543 (1995).
Cox et al., Chem. Rev., 95, pp. 1797–1842 (1995).

*Primary Examiner*—Zinna Northington Davis
(74) *Attorney, Agent, or Firm*—George W. Johnston; Patricia S. Rocha-Tramaloni

(57) ABSTRACT

A compound of the formula (I) wherein A, $R^1$, $R^2$ and X have the meanings defined in the specification, process of manufacturing such as compound and a pharmaceutical composition with HDAC inhibitor activity and anti-cell proliferation activity containing such a compound.

7 Claims, No Drawings

TETRAHYDROPYRIDINE DERIVATIVES, THEIR PREPARATION AND THEIR USE AS CELL PROLIFERATION INHIBITORS

The invention relates to tetrahydropyridine derivatives, or pharmaceutically-acceptable salts thereof, which possess anti-cell-proliferation activity such as anti-cancer activity and are accordingly useful in methods of treatment of the human or animal body. The invention also relates to processes for the manufacture of said tetrahydropyridine derivatives, to pharmaceutical compositions containing them and to their use in the manufacture of medicaments of use in the production of an anti-cell-proliferation effect in a warm-blooded animal such as man.

BACKGROUND OF THE INVENTION

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and apoptosis in several types of cancer cells, including colon cancer, T-cell lymphoma, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490–1495).

Several structural classes of HDAC inhibitors have been identified and are reviewed in Marks, P. M., J. Natl. Cancer Inst. 92 (2000) 1210–1216. More specifically, WO 98/55449 and U.S. Pat. No. 5,369,108 report alkanoyl hydroxamates with HDAC inhibitory activity.

It has now been found that certain tetrahydropyridine derivatives possess anti-cell-proliferation properties which are more potent than those in the aforementioned references. These properties are due to HDAC inhibition.

DESCRIPTION OF THE INVENTION

According to the invention there is provided a tetrahydropyridine derivative of the formula I

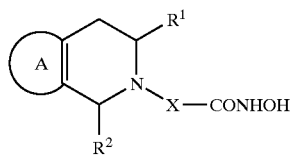

(I)

wherein

(a) denotes a phenyl group which may be unsubstituted or substituted with 1, 2 or 3 substituents independently selected from a halogen atom, an (1–4C)alkyl-, trifluoromethyl-, hydroxy-, (1–4C)alkoxy-, benzyloxy-, (1–3C)alkylenedioxy-, nitro-, amino-, (1–4C)alkylamino-, di[(1–4C)alkyl]-amino-, (1–4C) alkanoyl-amino-, or a phenyl group, which may be unsubstituted or substituted by 1, 2, or 3 substituents independently selected from a chlorine atom, an (1–4C) alkyl-, trifluoromethyl-, hydroxy-, (1–4C)alkoxy-, (1–3C)alkylenedioxy-, nitro-, amino-, (1–4C) alkylamino-, di[(1–4C)alkyl]amino-, and an (1–4C) alkanoylamino group, or (b) denotes an indolyl group which may be unsubstituted or substituted with 1, 2 or 3 substituents independently selected from a halogen atom, an (1–4C)alkyl-, trifluoromethyl-, hydroxy-, (1–4C)alkoxy-, benzyloxy-, (1–3C)alkylenedioxy-, nitro-, amino-, (1–4C)alkylamino-, di[(1–4C)alkyl]amino-, or an (1–4C)alkano-ylamino-group, $R^1$ and $R^2$ are the same as or different from each other and are a hydrogen atom, a (1–4C)alkyl-, a trifluoromethyl group, or an aryl group, X is a straight chain alkylene group comprising 5, 6, or 7 carbon atoms, wherein one $CH_2$ group may be replaced by an oxygen or a sulfur atom, or wherein 2 carbon atoms form a C=C double bond, and which is either unsubstituted or substituted by one or two substituents selected from (1–4C)alkyl and halogen atoms, their enantiomers, diastereoisomers, racemates and mixtures thereof and pharmaceutically acceptable salts.

A suitable value for a substituent when it is a halogen atom is, for example, fluoro, chloro, bromo and iodo; when it is (1–4C)alkyl is, for example, methyl, ethyl, propyl, isopropyl, butyl, isobutyl, sec-butyl; when it is (1–4C) alkoxy is, for example, methoxy, ethoxy, propoxy, isopropoxy or butoxy; when it is (1–4C)alkylamino is, for example, methylamino, ethylamino or propylamino; when it is di-[(1–4C)alkyl]amino is, for example, dimethylamino, N-ethyl-N-methylamino, diethylamino, N-methyl-N-propylamino or dipropylamino; when it is (1–4C) alkanoylamino is, for example, formylamido, acetamido, propionamido or butyramido; and when it is (1–3C) alkylenedioxy is, for example, methylenedioxy, ethylenedioxy or propylenedioxy.

A suitable pharmaceutically-acceptable salt of a tetrahydropyridine derivative of the invention is, for example, an acid-addition salt with, for example, an inorganic or organic acid, for example hydrochloric, hydrobromic, sulphuric, phosphoric, trifluoroacetic, citric or maleic acid.

The annulated tetrahydropyridine ring systems are preferably 3,4-dihydro-1H-isoquinoline or 1,3,4,5-tetrahydro-pyrido[4,3-b]indole or 1,3,4,9-tetrahydro-β-carboline.

Preferred compounds of the invention are tetrahydropyridine derivatives of the formula I

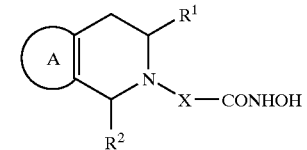

wherein

is a phenyl group which may be unsubstituted or substituted with 1 or 2 substituents independently chosen from hydroxy-, (1–4C)alkoxy, benzyloxy, or a phenyl group, or 

is an indolyl group which may be unsubstituted or substituted with a halogen atom, $R^1$ and $R^2$ are the same as or different from each other and are a hydrogen atom, a (1–4C)alkyl-, a trifluoromethyl group or a phenyl group, X is a straight chain alkylene group comprising 5, 6, or 7 carbon atoms, wherein one $CH_2$ group may be replaced by an oxygen or a sulfur atom, or wherein 2 carbon atoms form a C=C double bond, and which is either unsubstituted or substituted by one or two substituents selected from a methyl group, fluorine, or chlorine atoms, their enantiomers, diastereoisomers, racemates and mixtures thereof and pharmaceutically acceptable salts.

Preparation of the Compounds of the Invention

The tetrahydropyridine derivatives of the formula I, or a pharmaceutically-acceptable salt thereof, may be prepared by any process known to be applicable to the preparation of chemically-related compounds. Such processes, when used to prepare a tetrahydropyridine derivative of the formula I, or a pharmaceutically-acceptable salt thereof, are provided as a further feature of the invention and are illustrated by the following representative examples in which, unless otherwise stated, A, $R^1$, $R^2$ and X have any of the meanings defined hereinbefore. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

(a) One preferred method for the preparation of compounds of the formula I is the deprotection of compounds of the formula II

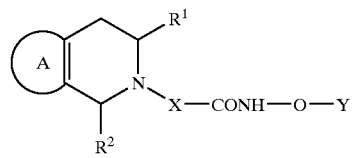

wherein Y is a suitable protecting group. Compounds of the formula II are new and included in the present invention.

Suitable protecting groups are the benzyl-, p-methoxybenzyl-, tert.butyloxycarbonyl-, trityl-, or silyl groups such as the trimethylsilyl- or dimethyl-tertbutylsilyl- group. The reactions carried out depend on the type of the protecting group. When the protecting group is a benzyl- or p-methoxybenzyl group, the reaction carried out is a hydrogenolysis in an inert solvent such as an alcohol like methanol or ethanol, in the presence of a noble metal catalyst such as palladium on a suitable carrier such as carbon, barium sulfate, or barium carbonate, at ambient temperature and pressure. When the protecting group is the tertbutyloxycarbonyl-, trityl-, or a silyl group such as the trimethylsilyl- or dimethyl-tert.butylsilyl-group, the reaction is carried out in the presence of acids at a temperature between −20° C. and 60° C., preferably between 0° C. and ambient temperature. The acid may be a solution of hydrochloric acid in an inert solvent such as diethyl ether or dioxane, or trifluoro acetic acid in dichloromethane. When the protecting group is a silyl group such as the trimethylsilyl or dimethyl-tert.butylsilyl group, the reaction is carried out in the presence of a fluoride source such as sodium fluoride or tetrabutyl ammonium fluoride in an inert solvent such as dichloromethane.

The tetrahydropyridine derivative of the formula I may be obtained from this process in the form of the free base or alternatively it may be obtained in the form of a salt. When it is desired to obtain the free base from the salt, the salt may be treated with a suitable base, for example, an alkali or alkaline earth metal carbonate or hydroxide, for example sodium carbonate, potassium carbonate, calcium carbonate, sodium hydroxide or potassium hydroxide.

Compounds of the formula II are obtained by the reaction of a tetrahydropyridine of the formula III

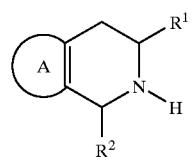

wherein A, $R^1$ and $R^2$ have the meaning defined hereinbefore, with a compound of formula IV

Z—X—CONH—O—Y      (IV)

wherein Z is a displaceable group and X and Y have the meaning defined hereinbefore, in the absence or presence of a suitable base.

A suitable displaceable group Z is, for example, a halogeno, or sulphonyloxy group, for example a chloro, bromo, methanesulphonyloxy or toluene-p-sulphonyloxy group. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-ethylpyrrolidin-2-one or dimethylsulphoxide. The reaction is conveniently carried out at a temperature in the range, for example, 10 to 250° C., preferably in the range 40–200° C.

(b) Another preferred method for the preparation of compounds of the formula I involves the reaction of compounds of the formula V

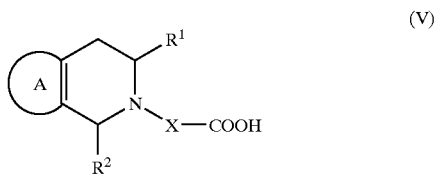

wherein A, $R^1$, $R^2$, and X have the meaning defined hereinbefore, with hydroxylamine. This reaction typically involves a two-step one-pot procedure. In the first step, the carboxylate of the formula V becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide. The reaction is carried out between −30° C. and 60° C., conveniently at or below 0° C. In the second step, hydroxylamine is added to the solution, at the temperature used for the activation, and the temperature is slowly adjusted to ambient temperature.

Compounds of the formula V are prepared from compounds of the formula VI

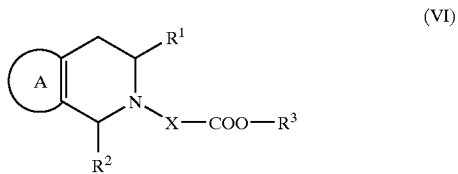

wherein A, $R^1$, $R^2$, and X have the meaning defined hereinbefore and $R^3$ is an alkyl group, for example, a methyl, ethyl, or tert. butyl group or benzyl group, by hydrolysis.

The conditions under which the hydrolysis is carried out depend on the nature of the group $R^3$. When $R^3$ is a methyl or ethyl group, the reaction is carried out in the presence of a base, for example, lithium hydroxide, sodium hydroxide, or potassium hydroxide in an inert solvent or diluent, for example, in methanol or ethanol. When $R^3$ is the tert.butyl group, the reaction is carried out in the presence of an acid, for example, a solution of hydrochloric acid in an inert solvent such as diethyl ether or dioxane, or trifluoro acetic acid in dichloromethane. When $R^3$ is the benzyl group, the reaction is carried out by hydrogenolysis in the presence of a noble metal catalyst such as Palladium on a suitable carrier, such as carbon.

Compounds of the formula VI are prepared from compounds of the formula III

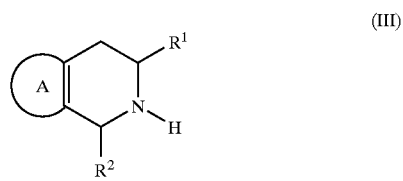

wherein A, $R^1$, and $R^2$ have the meaning defined hereinbefore, by reaction of compounds of the formula VII

Z—X—COO—$R^3$ (VI)

wherein Z, X, and $R^3$ have the meaning defined hereinbefore, in the absence or presence of a suitable base.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-ethylpyrrolidin-2-one or dimethylsulphoxide. The reaction is conveniently carried out at a temperature in the range, for example, 10 to 250° C., preferably in the range 40–200° C.

The compounds of formula III can be prepared by established methods, e.g. according to Hoshino, O., et al., In: The Chemistry of Heterocyclic Compounds; E. C. Taylor, ed., Volume 38, part 3, page 225 et seq., Wiley, N.Y. (1995); or according to Cox, E. D., and Cook, J. M., Chem. Rev. 95 (1995) 1797–1842; or Badia, D., et al., Trends Heterocycl. Chem. 2 (1991) 1–11.

(c) A third preferred method for the production of compounds of the formula I involves the reaction of compounds of the formula VIII

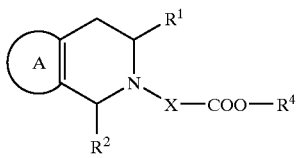

(VIII)

wherein A, $R^1$, $R^2$, and X have the meaning defined hereinbefore and $R^4$ is an (1–4C)alkyl group, for example, a methyl or ethyl group, with hydroxylamine in the presence of a suitable base.

The reaction is carried out in an inert solvent or diluent such as methanol or ethanol at temperatures between 0° C. and 100° C., conveniently at or near ambient temperature, and at a pH between 9 and 11. A suitable base is, for example, an alcoholate, for example, sodium methylate.

(d) Those compounds of the formula I wherein one of the substituents is an amino group are prepared by the reduction of a derivative of the formula I wherein the substituent is a nitro group. The reduction may conveniently be carried out by any of the many procedures known for such a transformation. The reduction may be carried out, for example, by the hydrogenation of a solution of the nitro compound in an inert solvent or diluent as defined hereinbefore in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50 to 150° C., conveniently at or near 70° C.

(e) Those compounds of the formula I wherein one of the substituents is an (1–4C)alkanoylamino group, are prepared by acylation of a derivative of the formula I wherein the substituent is an amino group. A suitable acylating agent is, for example, any agent known in the art for the acylation of amino to acylamino, for example an acyl halide, for example an alkanoyl chloride or bromide, conveniently in the presence of a suitable base, as defined hereinbefore, an alkanoic acid anhydride or mixed anhydride, for example acetic anhydride or the mixed anhydride formed by the reaction of an alkanoic acid and an alkoxycarbonyl halide, for example an alkoxycarbonyl chloride, in the presence of a suitable base as defined hereinbefore. In general the acylation is carried out in a suitable inert solvent or diluent as defined hereinbefore and at a temperature, in the range, for example, −30 to 120° C., conveniently at or near ambient temperature.

According to a further aspect of the invention there is provided a pharmaceutical composition which comprises a tetrahydropyridine derivative of the formula I, or a pharmaceutically-acceptable salt thereof, as defined hereinbefore in association with a pharmaceutically-acceptable diluent or carrier. The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a manner using conventional excipients. The tetrahydropyridine will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a tetrahydropyridine derivative of the formula I as defined hereinbefore for use in a method of treatment of the human or animal body by therapy. It was surprisingly found that the compounds of the present invention possess anti-cell-proliferation properties which are believed to arise from their histone deacetylase inhibitory activity. Accordingly the compounds of the present invention provide a method for treating the proliferation of malignant cells. Accordingly the compounds of the present invention are useful in the treatment of cancer by providing an anti-proliferative effect, particularly in the treatment of cancers of the breast, lung, colon, rectum, stomach, prostate, bladder, pancreas and ovary. In addition, the compounds according to the present invention will possess activity against a range of leukemias, lymphoid malignancies and solid tumors such as carcinomas and sarcomas in tissues such as the liver, kidney, prostate and pancreas.

Thus according to this aspect of the invention there is provided the use of a tetrahydropyridine derivative of the formula I, or a pharmaceutically-acceptable salt thereof, as defined hereinbefore in the manufacture of a medicament for use in the production of an anti-cell-proliferation effect in a warm-blooded animal such as man.

According to a further feature of this aspect of the invention there is provided a method for producing an anti-cell-proliferation effect in a warm-blooded animal, such as man, in need of such treatment which comprises administering to said animal an effective amount of a tetrahydropyridine derivative as defined hereinbefore.

The anti-cell-proliferation treatment defined hereinbefore may be applied as a sole therapy or may involve, in addition to the compounds of the invention, one or more other anti-tumor substances, for example those selected from, for example, mitotic inhibitors, for example vinblastine; alkylating agents, for example cis-platin, carboplatin and cyclophosphamide; inhibitors of microtubule assembly, like paclitaxel or other taxanes; antimetabolites, for example 5-fluorouracil, capecitabine, cytosine arabinoside and hydroxyurea, or, for example, intercalating antibiotics, for example adriamycin and bleomycin; immunostimulants, for example trastuzumab; DNA synthesis inhibitors, e.g. gemcitabine; enzymes, for example asparaginase; topoisomerase inhibitors, for example etoposide; biological response modifiers, for example interferon; and anti-hormones, for example antioestrogens such as tamoxifen or, for example antiandrogens such as (4'-cyano-3-(4-fluorophenylsulphonyl)-2-hydroxy-2-methyl-3'-(trifluoromethyl)-propionanilide, or other therapeutic agents and principles as described in, for example, DeVita, V. T., Jr., Hellmann, S., Rosenberg, S. A.; In: Cancer: Principles & Practice of Oncology, 5$^{th}$ ed., Lippincott-Raven Publishers (1997). Such conjoint treatment may be achieved by way of the simultaneous, sequential or separate dosing of individual components of the treatment. According to this aspect of the invention there is provided a pharmaceutical product comprising a tetrahydropyridine derivative of the formula I as defined hereinbefore and an additional anti-tumor substance as defined hereinbefore for the conjoint treatment of cancer.

The invention will now be illustrated in the following non-limiting examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) column chromatography (by the flash procedure) and high pressure liquid chromatography (HPLC) were performed on Merck Kieselgel silica or Merck Lichroprep RP-18 reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Kofler hot plate apparatus;

(vi) the structures of the end-products of the formula I were confirmed by nuclear (generally proton) magnetic resonance (NMR) and mass spectral techniques (Micromass Platform II machine using APCI or Micromass Platform ZMD using electrospray);

(vii) intermediates were not generally fully characterized and purity was assessed by thin layer chromatography.

EXAMPLE 1

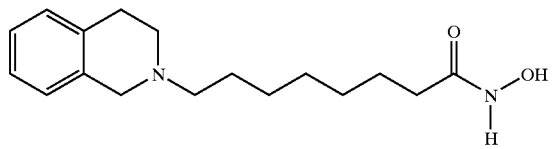

8-(3,4-Dihydro-1H-isoquinolin-2-yl)-octanoic acid hydroxyamide (a) In an ice bath, 14 ml triethylamine was added to a suspension of 3.2 g (20 mmol) O-benzylhydroxylamine hydrochloride in 150 ml dichloromethane. Stirring was continued until the solution became clear. Then, 4.5 g (20 mmol) omega-bromo octanoic acid was added, followed by 5.6 g (22 mmol) bis-(2-oxo-3-oxazolidinyl)-phosphorylchloride. Stirring was continued at ambient temperature for 18 h. The solution was extracted twice with 150 ml each of 1M aqueous hydrochloric acid and twice with 150 ml each of 1M aqueous sodium bicarbonate. The organic solvent was removed i. vac. to give 5.1 g (78%) of 8-bromo-octanoic acid benzyloxy-amide as a colorless oil. MS: 330 (M+H$^+$).

(b) A solution of 0.39 ml (3.12 mmol) 1,2,3,4-tetrahydroisoquinoline, 1.08 g (3.3 mmol) 8-bromo-octanoic acid benzyloxy-amide, and 0.46 g (3.3 mmol) potassium carbonate in 12 ml acetonitrile was heated to reflux for 2 h. After cooling to ambient temperature, water was added and extracted with ethyl acetate. The organic phase was washed with water, dried over sodium sulfate, filtered, and the solvent was evaporated. The residue was purified by reversed phase HPLC using methanol as eluent. There was thus obtained 1 g (84%) 8-(3,4-dihydro-1H-isoquinolin-2-yl)-octanoic acid benzyloxy-amide as a colorless oil. MS: 381 (M+H$^+$).

(c) 200 mg (0.53 mmol) 8-(3,4-dihydro-1H-isoquinolin-2-yl)-octanoic acid benzyloxy-amide in 30 ml methanol was hydrogenated for 1 h in the presence of palladium on barium sulfate at ambient temperature and pressure. The catalyst was removed by filtration and the solvent was evaporated. There was thus obtained 150 mg (98%) 8-(3,4-dihydro-1H-isoquinolin-2-yl)-octanoic acid hydroxyamide as an amorphous solid. MS: 291 (M+H$^+$).

EXAMPLE 2

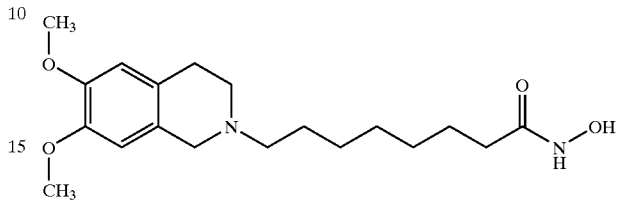

8-(6,7-dimethoxy-3,4-dihydro-1H-isoquinolin-2-yl)-octanoic acid hydroxyamide (a) In a manner analogous to that of example 1(b), 8-bromo-octanoic acid benzyloxy-amide (example 1(a); 0.3 g, 1.3 mmol) was reacted with 6,7-dimethoxy-1,2,3,4-tetrahydroisoquinoline hydrochloride (0.43 g, 1.3 mmol) in the presence of potassium carbonate (0.18 g, 1.4 mmol) and DMF as solvent to give 8-(6,7-dimethoxy-3,4-dihydro-1H-isoquinolin-2-yl)-octanoic acid benzyloxyamide as an almost colorless wax (yield 0.28 g, 49%; purified by column chromatography using silica gel and ethyl acetate: methanol 9:1 as an eluent). MS (M+H$^+$)=441.

(b) In a manner analogous to that of example 1(c), 8-(6,7-dimethoxy-3,4-dihydro-1H-isoquinolin-2-yl)-octanoic acid benzyloxyamide was hydrogenated to give the title compound in 98% yield as an amorphous solid. MS (M+H$^+$)=351.

EXAMPLE 3

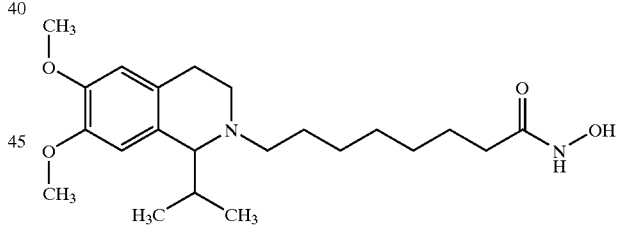

8-(1-isopropyl-6,7-dimethoxy-3,4-dihydro-1H-isoquinolin-2-yl)-octanoic acid hydroxyamide (a) In a manner analogous to that of example 1(b), 8-bromo-octanoic acid benzyloxy-amide (example 1(a); 0.3 g, 1.1 mmol) was reacted with 1-isopropyl-6,7-dimethoxy-1,2,3,4-tetrahydroisoquinoline hydrochloride (0.3 g, 1.1 mmol) in the presence of potassium carbonate (0.15 g, 1.1 mmol) and DMF as solvent to give 8-(1-isopropyl-6,7-dimethoxy-3,4-dihydro-1H-isoquinolin-2-yl)-octanoic acid benzyloxyamide as an almost colorless wax (yield 0.1 g, 20%; purified by column chromatography using silica gel and ethyl acetate as eluent). MS (M+H$^+$)=483.

(b) In a manner analogous to that of example 1(c), 8-(1-isopropyl-6,7-dimethoxy-3,4-dihydro-1H-isoquinolin-2-yl)-octanoic acid benzyloxyamide was hydrogenated to give the title compound as an amorphous solid. MS (M+H$^+$)=393.

EXAMPLE 4

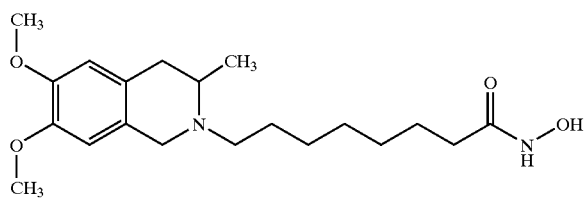

8-(6,7-dimethoxy-3-methyl-3,4-dihydro-1H-isoquinolin-2-yl)-octanoic acid hydroxyamide (a) In a manner analogous to that of example 1(b), 8-bromo-octanoic acid benzyloxy-amide (example 1(a); 0.7 g, 2.1 mmol) was reacted with 6,7-dimethoxy-3-methyl-1,2,3,4-tetrahydroisoquinoline hydrochloride (0.5 g, 2.1 mmol) in the presence of potassium carbonate (0.3 g, 2.2 mmol) and DMF as solvent to give 8-(6,7-dimethoxy-3-methyl-3,4-dihydro-1H-isoquinolin-2-yl)-octanoic acid benzyloxyamide as an almost colorless wax (yield 0.35 g, 37%; purified by column chromatography using silica gel and ethyl acetate: methanol=95:5 as an eluent). MS (M+H$^+$)=455.

(b) In a manner analogous to that of example 1(c), 8-(6,7-dimethoxy-3-methyl-3,4-dihydro-1H-isoquinolin-2-yl)-octanoic acid benzyloxyamide was hydrogenated to give the title compound in 98% yield as an almost colorless oil. MS (M+H$^+$)=365.

EXAMPLE 5

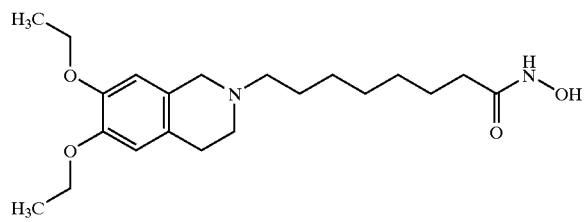

8-(6,7-Diethoxy-3,4-dihydro-1H-isoquinolin-2-yl)-octanoic acid hydroxyamide (a) In a manner analogous to that of example 1(b), 8-bromo-octanoic acid benzyloxy-amide (example 1(a); 0.38 g, 1.2 mmol) was reacted with 6,7-diethoxy-1,2,3,4-tetrahydroisoquinoline hydrochloride (0.3 g, 1.2 mmol) in the presence of potassium carbonate (0.16 g, 1.2 mmol) and DMF as solvent to give 8-(6,7-diethoxy-3,4-dihydro-1H-isoquinolin-2-yl)-octanoic acid benzyloxyamide as an almost colorless wax (yield 0.15 g, 27%; purified by column chromatography using silica gel and ethyl acetate: methanol=9:1 as an eluent). MS (M+H$^+$)=469.

(b) In a manner analogous to that of example 1(c), 8-(6,7-diethoxy-3,4-dihydro-1H-isoquinolin-2-yl)-octanoic acid benzyloxyamide was hydrogenated to give the title compound in 98% yield as an amorphous solid. MS (M+H$^+$)=379.

EXAMPLE 6

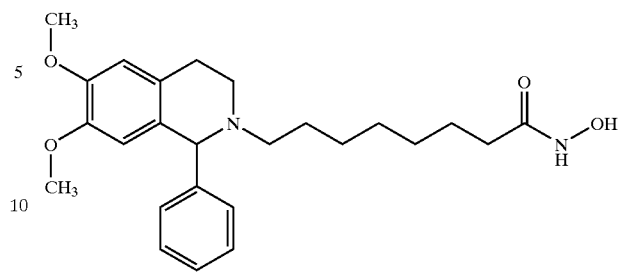

8-(6,7-dimethoxy-1-phenyl-3,4-dihydro-1H-isoquinolin-2-yl)-octanoic acid hydroxyamide (a) In a manner analogous to that of example 1(b), 8-bromo-octanoic acid benzyloxy-amide (example 1(a); 0.3 g, 1.1 mmol) was reacted with 6,7-dimethoxy-1-phenyl-1,2,3,4-tetrahydroisoquinoline hydrochloride (0.32 g, 1 mmol) in the presence of potassium carbonate (0.14 g, 1 mmol) and DMF as solvent to give 8-(6,7-dimethoxy-1-phenyl-3,4-dihydro-1H-isoquinolin-2-yl)-octanoic acid benzyloxyamide as an amorphous solid (yield 0.12 g, 23%; purified by column chromatography using silica gel and ethyl acetate: heptane=1:1 as an eluent). MS (M+H$^+$)=517.

(b) In a manner anologous to that of example 1(c), 8-(6,7-dimethoxy-1-phenyl-3,4-dihydro-1H-isoquinolin-2-yl)-octanoic acid benzyloxyamide was hydrogenated to give the title compound in 98% yield as an amorphous solid. (M+H$^+$)=427.

EXAMPLE 7

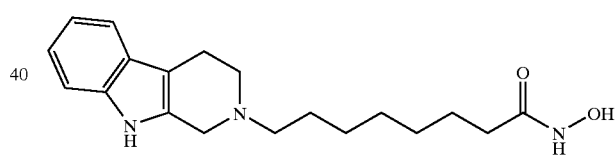

8-(1,3,4,9-tetrahydro-β-carbolin-2-yl)-octanoic acid hydroxyamide (a) In a manner analogous to that of example 1(b), 8-bromo-octanoic acid benzyloxy-amide (example 1(a); 0.5 g, 1.5 mmol) was reacted with 1,2,3,4-tetrahydro-9H-pyrido[3,4-b]indole (0.25 g, 1.4 mmol) in the presence of potassium carbonate (0.2 g, 1.4 mmol) and DMF as solvent to give 8-(1,3,4,9-tetrahydro-b-carbolin-2-yl)-octanoic acid benzyloxyamide as an amorphous solid (yield 0.18 g, 30%; purified by column chromatography using silica gel and ethyl acetate as eluent). MS (M+H$^+$)=420.

(b) In a manner anologous to that of example 1(c), 8-(1,3,4,9-tetrahydro-β-carbolin-2-yl)-octanoic acid benzyloxyamide was hydrogenated to give the title compound in 98% yield as an amorphous solid. MS (M+H$^+$)=330.

EXAMPLE 8

In an analogous manner to that described in the examples 1–7 the following compounds are prepared:

(a) 7-(3,4-Dihydro-1H-isoquinolin-2-yl)-heptanoic acid hydroxyamide

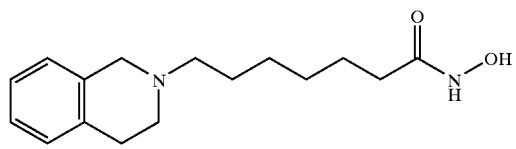

(b) 6-(3,4-Dihydro-1H-isoquinolin-2-yl)-hexanoic acid hydroxyamide

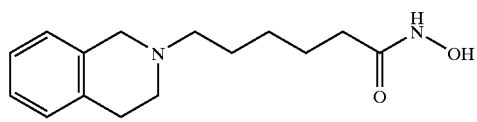

(c) 8-(3,4-Dihydro-6-phenyl-1H-isoquinoline-2-yl)-octanoic acid hydroxamide

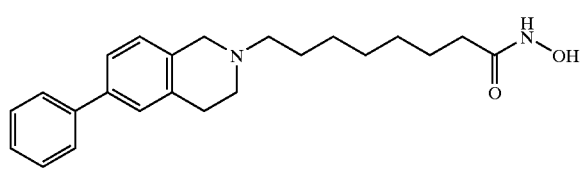

(d) 8-(3,4-Dihydro-7-phenyl-1H-isoquinolin-2-yl)-octanoic acid hydroxyamide

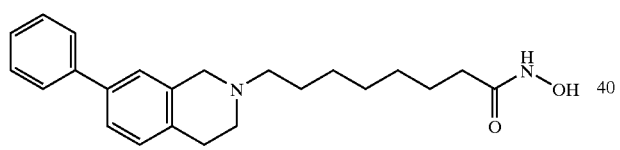

(e) 8-(1-Trifluoromethyl-1,3,4,9-tetrahydro-β-carbolin-2-yl)-octanoic acid hydroxyamide

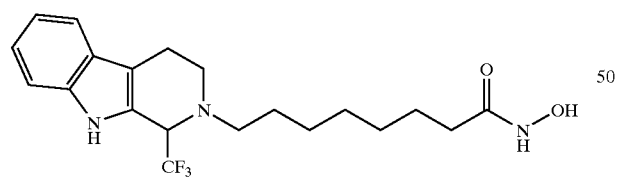

(f) 8-(6-Fluoro-1,3,4,5-tetrahydro-pyrido[4,3-b]indol-2-yl)-octanoic acid hydroxyamide

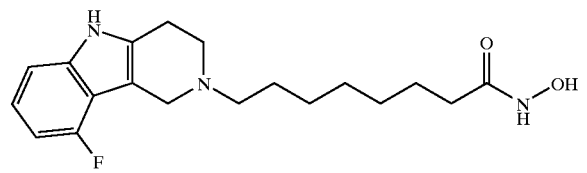

(g) 7-(3,4-Dihydro-1H-isoquinolin-2-yl)-5-methyl-heptanoic acid hydroxyamide

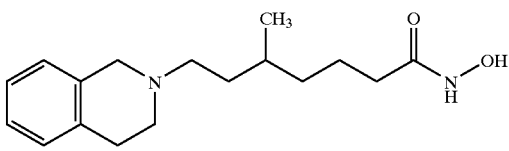

(h) 7-(3,4-Dihydro-1H-isoquinolin-2-yl)-4-methyl-heptanoic acid hydroxyamide

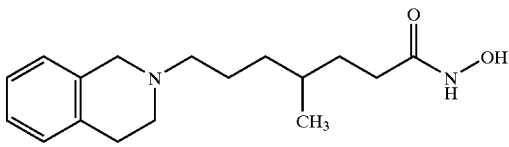

(i) 7-(3,4-Dihydro-1H-isoquinolin-2-yl)-3-methyl-heptanoic acid hydroxyamide

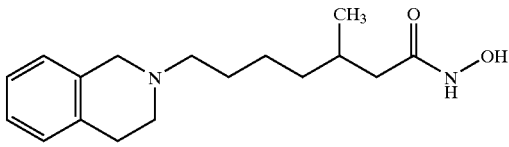

(j) 7-(3,4-Dihydro-1H-isoquinolin-2-yl)-2-methyl-heptanoic acid hydroxyamide

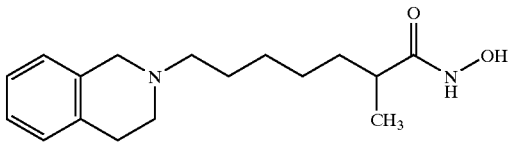

(k) 7-(3,4-Dihydro-1H-isoquinolin-2-yl)-2-chloro-heptanoic acid hydroxyamide

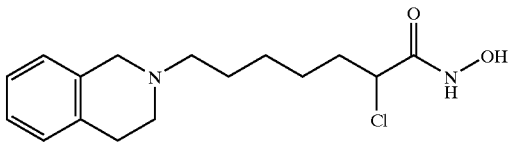

(l) 7-(3,4-Dihydro-1H-isoquinolin-2-yl)-2,2-dimethyl-heptanoic acid hydroxyamide

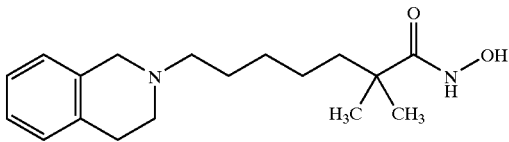

(m) 7-(3,4-Dihydro-1H-isoquinolin-2-yl)-2,2-dichloro-heptanoic acid hydroxyamide

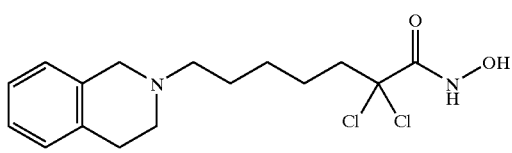

(n) 8-(3,4-Dihydro-1H-isoquinolin-2-yl)-2-methyl-octanoic acid hydroxyamide

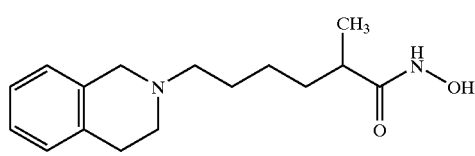

(o) 6-(3,4-Dihydro-1H-isoquinolin-2-yl)-2-methyl-hexanoic acid hydroxyamide

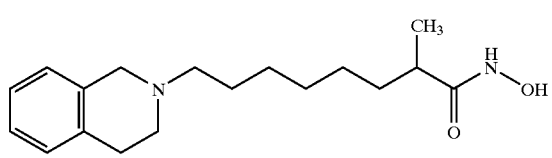

(p) 7-(3,4-Dihydro-1H-isoquinolin-2-yl)-4-oxa-heptanoic acid hydroxyamide

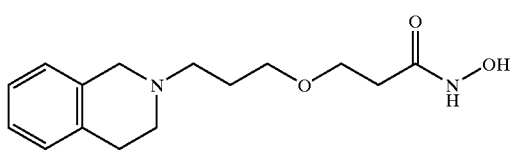

(q) 7-(3,4-Dihydro-1H-isoquinolin-2-yl)-3-methyl-4-oxa-heptanoic acid hydroxyamide

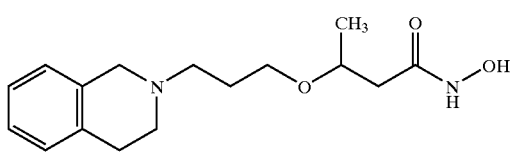

(r) 7-(3,4-Dihydro-1H-isoquinolin-2-yl)-3-oxa-heptanoic acid hydroxyamide

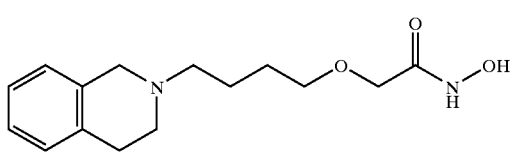

(s) 7-(3,4-Dihydro-1H-isoquinolin-2-yl)-3-oxa-5cis-heptenoic acid hydroxyamide

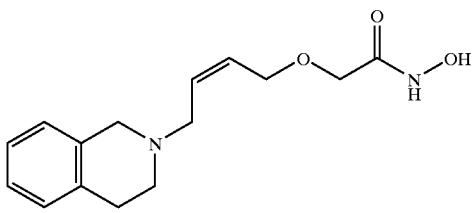

(t) 7-(3,4-Dihydro-1H-isoquinolin-2-yl)-3-oxa-5trans-heptanoic acid hydroxyamide

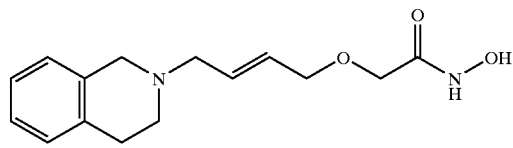

(u) 7-(3,4-Dihydro-1H-isoquinolin-2-yl)-2-methyl-3-oxa-heptanoic acid hydroxyamide

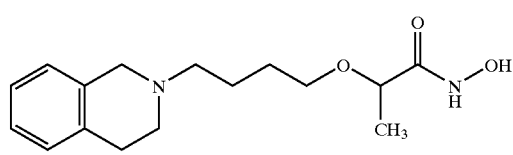

EXAMPLE 9

Evaluation of HDAC Inhibitory Properties of the Compounds of the Invention

To determine the HDAC inhibitory properties of the compounds of the invention an assay was performed using an aminocoumarin derivative of an omega-acetylated lysine as substrate for the enzyme. This assay has been described in detail by Hoffmann, K., et al., Nucleic Acids Res. 27 (1999) 2057–2058. Using the protocol described therein, the inhibitory effect of representative compounds was determined at a concentration of 10 nM. The observed inhibition rates for selected compounds are shown in Table 1:

TABLE 1

| Title compound of example No | Inhibitory effect at 10 nM in % |
|---|---|
| 1 | 54 |
| 5 | 26 |
| 6 | 26 |
| 7 | 26 |

List of References

Badia, D., et al., Trends Heterocycl. Chem. 2 (1991) 1–11
Cox, E. D., and Cook, J. M., Chem. Rev. 95 (1995) 1797–1842
DeVita, V. T., Jr., Hellmann, S., Rosenberg, S. A.; In: Cancer: Principles & Practice of Oncology, 5$^{th}$ ed., Lippincott-Raven Publishers (1997)
Hoffmann, K., et al., Nucleic Acids Res. 27 (1999) 2057–2058
Hoshino, O., et al., In: The Chemistry of Heterocyclic Compounds; E. C. Taylor, ed., Volume 38, part 3, page 225 et seq., Wiley, N.Y. (1995)
Koyama, Y., et al., Blood 96 (2000) 1490–1495
Marks, P. M., J. Natl. Cancer Inst. 92 (2000) 1210–1216
U.S. Pat. No. 5,369,108
WO 98/55449

What is claimed is:

1. A compound of formula I

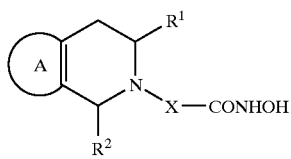

wherein

(a) denotes a phenyl group which may be unsubstituted or substituted with 1, 2 or 3 substituents independently selected from a halogen atom, an (1–4C)alkyl-, trifluoromethyl-, hydroxy-, (1–4)alkoxy-, benzyloxy-, (1–3C)alkylenedioxy-, nitro-, amino-, (1–4C) alkylamino-, di[(1–4C)alkyl]amino-, (1–4C)alkanoyl-amino-, or a phenyl group, which may be unsubstituted or substituted by 1, 2, or 3 substituents independently selected from a chlorine atom, an (1–4C)alkyl-, trifluoromethyl-, hydroxy-, (1–4C)alkoxy-, (1–3C) alkylenedioxy-, nitro-, amino-, (1–4C)alkylamino-, di[(1–4C)alkyl]amino-, and a (1–4C)alkanoylamino group, or (b) denotes an indolyl group which may be unsubstituted or substituted with 1, 2 or 3 substituents independently selected from a halogen atom, an (1–4C)alkyl-, trifluoromethyl-, hydroxy-, (1–4C)alkoxy-, benzyloxy-, (1–3C)alkylenedioxy-, nitro-, amino-, (1–4C)alkylamino-, di[(1–4C)alkyl]amino-, or a (1–4C)alkanoylamino-group, $R^1$ and $R^2$ are the same as or different from each other and are a hydrogen atom, an (1–4C)alkyl-, a trifluoromethyl group, or an aryl group, X is a straight chain alkylene group comprising 5, 6 or 7 carbon atoms, wherein one $CH_2$ group may be replaced by an oxygen or a sulfur atom, or wherein 2 carbon atoms form a C=C double bond, and which is either unsubstituted or substituted by one or two substituents selected from (1–4C)alkyl and halogen atoms, or a pharmaceutically acceptable salt thereof.

2. The compound of formula I according to claim 1 wherein

is a phenyl group which may be unsubstituted or substituted with 1 or 2 substituents independently chosen from hydroxy-, (1–4C)alkoxy, benzyloxy, or a phenyl group, or 

is an indolyl group which may be unsubstituted or substituted with a halogen atom, $R^1$ and $R^2$ are the same as or different from each other and are a hydrogen atom, a (1–4C)alkyl-, a trifluoromethyl group or a phenyl group, X is a straight chain alkylene group comprising 5, 6, or 7 carbon atoms, wherein one $CH_2$ group may be replaced by an oxygen or a sulfur atom, or wherein 2 carbon atoms form a C=C double bond, and which is either unsubstituted or substituted by one or two substituents selected from a methyl group, fluorine, or chlorine atoms, or a pharmaceutically acceptable salts.

3. The compound of formula I according to claim 1 selected from the group consisting of 8-(3,4-Dihydro-1H-isoquinolin-2-yl)-octanoic acid hydroxyamide;

8-(6,7-dimethoxy-3,4-dihydro-1H-isoquinolin-2-yl)-octanoic acid hydroxyamide;

8-(1-isopropyl-6,7-dimethoxy-dihydro-1H-isoquinolin-2-yl)-octanoic acid hydroxyamide;

8-(6,7-dimethoxy-3-methyl-3,4-dihydro-1H-isoquinolin-2-yl)-octanoic acid hydroxyamide;

8-(6,7-diethoxy-3,4-dihydro-1H-isoquinolin-2-yl)-octanoic acid hydroxyamide;

8-(6,7-dimethyl-1-phenyl-3,4-dihydro-1H-isoquinolin-2-yl)-octanoic acid hydroxyamide; and 8-(1,3,4,9-tetrahydro-β-carbolin-2-yl)-octanoic acid hydroxyamide.

4. A process of manufacturing a compound of formula I according to claim 1 by reacting a compound of formula III

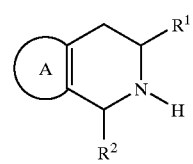

wherein A, $R^1$ and $R^2$ have the meaning defined in claim 1 with a compound of formula IV

wherein Z is a displaceable group, Y is a protecting group and X has the meaning as defined in claim 1, in the presence of a suitable base, where after the protecting group Y is splitted off by hydrogenolysis.

5. A pharmaceutical composition containing as active ingredient a compound of formula I according to claim 1 in admixture with a pharmaceutically acceptable excipient or diluent.

6. The compound of claim 1 wherein the compound is an enantiomer, diastercoisomer or mixtures thereof.

7. A method of treating a disease based on histone deacetylase inhibitor activity comprising administering to a patient in need of such treatment a therapeutically effective amount of at least one compound of formula I

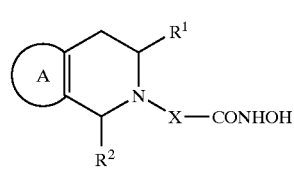

wherein

(a) denotes a phenyl group which may be unsubstituted or substituted with 1, 2 or 3 substituents independently selected from a halogen atom, an (1–4C)alkyl-, trifluoromethyl-, hydroxy-, (1–4C)alkyl-, benzyloxy-, (1–3C)alkylenedioxy-, nitro-, amino-, (1–4C) alkylamino-, di[(1–4C)alkyl]-amino-, (1–4C)alkanoyl-amino, or a phenyl group, which may be unsubstituted or substituted by 1, 2, or 3 substituents independently selected from a chlorine atom, an (1–4C)alkyl-, trifluoromethyl-, hydroxy-, (1–4C)alkoxy-, (1–3C) alkylenedioxy-, nitro-, amino-, (1–4C)alkylamino-, di[(1–5C)alkyl]amino-, and a (1–4C)alkanoylamino group, or (b) denotes an indolyl group which may be unsubstituted or substituted with 1, 2 or 3 substituents independently selected from a halogen atom, an (1–4C)alkyl-, trifluoromethyl-, hydroxy-, (1–4C)alkyl-, benzyloxy-, (1–3C)alkylenedioxy-, nitro-, amino-, (1–4C) alkylamino-, di[(1–C)alkyl]amino-, or a (1–4C) alkanoylamino-group, $R^1$ and $R^2$ are the same as or different from each other and are a hydrogen atom, an (1–4C)alkyl-, trifluoromethyl group, or an aryl group, X is a straight chain alkylene group comprising 5, 6 or 7 carbon atoms, wherein one $CH_2$ group may be replaced by an oxygen or a sulfur atom, or wherein 2 carbon atoms form a C=C double bond, and which is either unsubstituted or substituted by one or two substituents selected from (1–4C)alkyl and halogen atoms, or a pharmaceutically acceptable salt thereof.

* * * * *

UNITED STATES PATENT AND TRADEMARK OFFICE
CERTIFICATE OF CORRECTION

PATENT NO. : 6,800,638 B2
APPLICATION NO. : 10/451757
DATED : October 5, 2004
INVENTOR(S) : Guy Georges et al.

It is certified that error appears in the above-identified patent and that said Letters Patent is hereby corrected as shown below:

On the title page item (75), Inventors, delete "Grossman, Eglfing (DE): Olaf" and insert -- Grossmann, Eglfing (DE): Olaf --.

On the title page item (73), Assignee, delete "Hoffman-La Roche Inc." and insert -- Hoffmann-La Roche Inc. --.

Signed and Sealed this

Twenty-sixth Day of January, 2010

David J. Kappos
*Director of the United States Patent and Trademark Office*